United States Patent
Roelvink et al.

(10) Patent No.: US 10,139,468 B2
(45) Date of Patent: Nov. 27, 2018

(54) PLANAR TRANSMISSION-LINE PERMITTIVITY SENSOR AND CALIBRATION METHOD FOR THE CHARACTERIZATION OF LIQUIDS, POWDERS AND SEMISOLID MATERIALS

(71) Applicant: The United States of America, as represented by the Secretary of Agriculture, Washington, DC (US)

(72) Inventors: Jochem T. Roelvink, Auckland (NZ); Samir Trabelsi, Watkinsville, GA (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/839,083

(22) Filed: Aug. 28, 2015

(65) Prior Publication Data

US 2016/0187402 A1  Jun. 30, 2016

Related U.S. Application Data

(60) Provisional application No. 62/043,659, filed on Aug. 29, 2014.

(51) Int. Cl.
*G01R 35/00* (2006.01)
*G01N 22/00* (2006.01)

(52) U.S. Cl.
CPC .......... *G01R 35/005* (2013.01); *G01N 22/00* (2013.01)

(58) Field of Classification Search
CPC .. G01R 27/22; G01R 27/2617; G01R 35/005; G01N 33/00; G01N 22/00

USPC .................................................. 324/637–647
See application file for complete search history.

(56) References Cited

U.S. PATENT DOCUMENTS

| | | | | |
|---|---|---|---|---|
| 6,975,199 | B2* | 12/2005 | Long ...................... | H01F 5/003 257/E27.046 |
| 7,741,943 | B2* | 6/2010 | Fouquet .............. | H01F 27/2804 336/200 |
| 2001/0019271 | A1* | 9/2001 | Scott ...................... | G01N 22/00 324/637 |
| 2007/0008060 | A1* | 1/2007 | Weller ................. | G01N 27/023 336/229 |
| 2007/0176827 | A1* | 8/2007 | Itoh ...................... | H01Q 13/206 343/700 MS |
| 2008/0036469 | A1* | 2/2008 | Chladek ............... | G01R 35/005 324/601 |
| 2009/0134885 | A1* | 5/2009 | Hayashi ................. | G01R 31/36 324/663 |
| 2009/0322350 | A1* | 12/2009 | Aygun ............... | G01R 31/2818 324/642 |
| 2010/0001742 | A1* | 1/2010 | Strid .................... | G01R 35/005 324/601 |
| 2010/0182096 | A1* | 7/2010 | Kim ......................... | H01P 5/10 333/26 |
| 2011/0304516 | A1* | 12/2011 | Ko ........................... | H01Q 1/38 343/722 |

\* cited by examiner

*Primary Examiner* — Jeff Natalini
(74) *Attorney, Agent, or Firm* — John Fado; Gail Poulos

(57) ABSTRACT

A low cost planar transmission line sensor and simple calibration method for measuring the complex permittivity of materials with minimal sample preparation over a wide band of radio- and microwave frequencies. The sensor is also used for measuring anisotropic dielectric properties of materials with a defined grain.

2 Claims, 11 Drawing Sheets

PLANAR TRANSMISSION-LINE PERMITTIVITY SENSOR AND CALIBRATION METHOD FOR THE CHARACTERIZATION OF LIQUIDS, POWDERS AND SEMISOLID MATERIALS

REFERENCE TO RELATED APPLICATIONS

This application claims the benefit of U.S. Provisional Patent Application Ser. No. 62/043,659, filed Aug. 29, 2014 entitled "Permittivity Planar Transmission-Line Sensor and Calibration Method for the Characterization of Liquids, Powders, and Semisolid Materials". The U.S. Provisional Patent Application Ser. No. 62/043,659 is herein incorporated by reference in its entirety.

FIELD OF THE INVENTION

The present invention relates to a sensor apparatus and a calibration method for measuring the complex permittivity of liquids, powders, and semisolid materials with planar transmission lines at radio- and microwave-frequencies. Furthermore the present invention relates to a method for measuring the anisotropic dielectric properties of materials with the sensor apparatus.

BACKGROUND OF THE INVENTION

The permittivity of a material describes the relationship between electric flux density and an applied electric field. Permittivity is a function of frequency and the physical and molecular properties of any material. If a relationship between the material permittivity and a physical property of interest can be established, permittivity measurements can be used to infer the measurement of several attributes of, for example, agricultural and food materials, solvents, pharmaceutical materials. This has been used successfully in the measurement of several attributes of agricultural products such as, for example, the water content of grain (Trabelsi and Nelson, IEEE Trans. On Instrumentation and Measurement, Volume 55 (3), 953-963, 2006; Nelson and Trabelsi, Trans. ASABE, Volume 55 (2), 629-636, May 2012; Kraszewski et al., Meas. Sci. Technol., Volume 8, 857-863, 1990), and the fat content of fish (Kent, Food Control, Volume 1, 47-53, 1990). More recently (Duhamel et al., Proc. IEEE MTT-S Int. Microwave Sym. Dig., Denver, Colo., USDA, 107-110, 1997; Joines et al., Me. Phys., Volume 21, 547-550, April 1994; Trabelsi and Nelson, American Society of Agricultural and Biological Engineers, St. Joseph, Mich., ASABE Paper No. 097305, 2009; Trabelsi and Roelvink, Journal of Microwave Power and Electromagnetic Energy, Volume 48 (4), 215-220, 2014), there has been a focus on using the permittivity of biological materials to identify physical properties such as healthy or diseased human breast tissue (Joines et al., April 1994, supra), or the quality attributes of poultry meat (Trabelsi and Nelson, 2009, supra).

The complex relative permittivity of a material, $\varepsilon^*$, is an intrinsic electrical property that relates the electric flux density within the material to an applied electric field. The relative complex permittivity is often written as $\varepsilon^*=\varepsilon'-j\varepsilon''$, where $\varepsilon'$ is the dielectric constant and $\varepsilon''$ is the dielectric loss factor. The permittivity (or dielectric properties) is a function of the physical properties of a material, such as the moisture and density of granular and particulate materials. If a relationship between the permittivity and a physical property of interest can be established, permittivity measurements can be used as an indirect, non-destructive method of inferring physical properties. In industrial RF and microwave heating applications, the knowledge of the permittivity of the material to be heated allows rigorous analytical and numerical design of heating cavities and other electromagnetic heating apparatus. The development of sensors and techniques for accurately and efficiently measuring the permittivity of agricultural and biological materials is therefore an area of research with significant commercial potential.

Relationships between the physical and dielectric properties of materials have been reported in several previous studies. Examples for agricultural products are sensors for measuring the water content of grain (Nelson and Trabelsi, ASABE, Volume 55(2), 629-636, 2012), or the fat content of fish (Kent, Food Control, Volume 1, 47-53, 1990). Examples for biological materials are methods for inferring quality attributes of poultry meat (Trabelsi and Nelson, ASABE Paper No. 097305, American Society of Agricultural and Biological Engineers, 2009) or differences between normal and diseased human breast tissue (Joines et al., 1994, supra). The permittivity of biological tissue such as poultry meat depends on a number of factors related to the quality parameters, such as water holding capacity and pH (Trabelsi and Nelson, 2009, supra; Trabelsi, American Society of Agricultural and Biological Engineers, 2012, ASABE Paper No. 121337363). Such properties can vary over a given sample volume, thus the permittivity of poultry meat is often heterogeneous and anisotropic (Clerjon and Damez, Meas. Sci. Technol., Volume 18, 1038-1045, 2007). The degree of anisotropy is a parameter that can be used to estimate parameters such as tissue age (Damez et al, Journal of Food Engineering, Volume 85, 116-122, 2008) or the difference between fresh and frozen meat (Clerjon and Damez, 2007, supra). A convenient measurement method for characterizing dielectric anisotropy of materials would be very useful.

Many techniques have been developed for determining the permittivity of materials (Baker-Jarvis et al., IEEE Trans. Microwave Theory Tech., Volume 38 (8), 1096-1103, August, 1990; Pournaropoulos and Misra, Meas. Sci. Technol., Volume 8 (11), 1191-1202, 1997; Knöchel et al., Meas. Sci. Technol., Volume 18 (4), 1061-1068, 2007; Baker-Jarvis et al., NIST Tech. Note 1536, 2005), some of which have been implemented as industrial sensors (Nyfors and Vainikainen, Industrial Microwave Sensors. Norwood, Mass., USA: Artech House, 1989). Perhaps the most commonly utilized modern method for measuring the permittivity of liquids involves the use of an open-ended coaxial-line probe (Pournaropoulos and Misra, 1997, supra). Its popularity is largely due to relatively simple calibration procedures (Kraszewski et al., IEEE Trans. Instrum. Meas., Volume 32 (2), 385-387, June 1983), its ability to measure over a wide range of frequencies, and its commercial availability (Agilent-Technologies, Agilent 85070E Dielectric Probe Kit: 200 MHz to 50 GHz Technical Overview). However, to measure the permittivity of water-based materials, which have relatively large dielectric constants, the coaxial-line probe must be relatively small to avoid radiation effects (Wei and Sridhar, Proc. IEEE MTT-S Int. Microwave Symp. Dig., Albuquerque, N. Mex., USA, 1271-1274, 1992; Wei and Sridhar, IEEE Trans. Microwave Theory Tech., Volume 39 (3), 526-531, March 1991). Therefore, for biological materials, only a small volume of material can be measured (Hagl et al., IEEE Trans. Microwave Theory Tech., Volume 51 (4), 1194-1206, April 2003). In addition, the open-ended coaxial-line probe cannot be conveniently used to characterize the dielectric anisotropy of materials, (Clerjon and Damez, Meas. Sci. Technol., Volume 18, 1038-1045, 2007).

Transmission lines are often used to measure the broadband complex permittivity of liquid and semisolid materials (Baker-Jarvis et al., IEEE Trans. Microwave Theory Tech., Volume 38, 1096-1103, 1990). The measurement is typically made by placing the material in a section of transmission line and measuring the two-port complex scattering parameters over a range of frequencies. The complex line propagation constant, $\gamma$, can be obtained from the scattering parameters by various methods. The complex relative permittivity of the material can then be found from a model that relates $\varepsilon^*$ to $\gamma$. This model is dependent on the transmission-line dimensions and type, e.g., waveguide, coaxial line, planar line. Compared to the open-ended coaxial-line probe, these transmission line arrangements offer the advantage of measuring the average permittivity of the material along the length of line. The sensing length, and therefore the material volume, can be large relative to volumes sensed by open-ended coaxial-line probes. However, the closed structures of many of these transmission line types, (e.g., waveguide and coaxial line) mean that considerable sample preparation is necessary. Closed transmission lines cannot be conveniently used to measure the permittivity of materials outside a laboratory.

Planar transmission lines, such as coplanar waveguide (CPW), can be configured as permittivity sensors (Stuchly and Bassey, Meas. Sci. Technol., Volume 9, 1324-1329, 1998). The open structure of these transmission lines requires relatively less sample preparation compared to closed transmission-line types because the sample material can be easily placed in contact with the lines without needing to mechanically connect a section of sample-filled transmission line. To numerically extract $\varepsilon^*$ from $\gamma$, either closed-form approximations for the CPW parameters (Roelvink and Trabelsi, IEEE Trans. Instr. Meas., Volume 62 (11), 2974-2982, 2013; herein incorporated by reference in its entirety) or full-wave numerical techniques can be applied (Huynen et al., IEEE Trans. Microwave Theory Tech., Volume 42 (11), 2099-2106, 1994). However, a significant limitation of these approaches is that neither allows $\varepsilon^*$ to be directly calculated from $\gamma$, and numerical iterative methods must be used. Moreover, it has been demonstrated for planar line parameters (Roelvink and Trabelsi, IEEE Trans. Instr. Meas., 2013, supra), that the $\varepsilon^*$ extracted from such an approach is very sensitive to the line dimensions, particularly for materials with relatively large dielectric constants, such as water-based biological materials. A small uncertainty in these dimensions can result in considerable uncertainty in the measured $\varepsilon^*$. If the planar lines are fabricated with low-cost equipment, the dimensional uncertainty is often large. For such situations an alternative approach such as a calibration procedure for extracting $\varepsilon^*$ that does not required a precise knowledge of the line dimensions would be very useful.

Existing methods for measuring the permittivity tensor of materials with anisotropic dielectric properties generally operate by placing a sample in a section of waveguide or coaxial transmission line and measuring the two-port scattering parameters with the sample 'grain' oriented in two ways; parallel and perpendicular to the transverse electric field component of the propagating wave (Akhtar et al., IEEE Trans. Microwave Theory Tech., Volume 54, 2011-2022, 2006; Torgovnikov, *Dielectric Properties of Wood and Wood-Based materials*, Wood Science, ed. Timell, 1993, Berlin: Springer-Verlag). These methods require that the sample be carefully prepared and are mechanically time consuming. Moreover, for biological materials such as muscle tissue, it can be difficult to precisely identify the direction of the grain. If the sample is not properly aligned, this approach does not provide an accurate measurement of the permittivity tensor. The high level of precision means that such an approach is not well suited to measurements outside the laboratory.

There have been a number of studies that use planar or strip transmission lines to measure permittivity. Stuchly and Bassey (1998, supra) investigated the use of CPW for measuring $\varepsilon'$. In their study, $\varepsilon'$ was determined by a technique that did not account for the source and load mismatch terms associated with the line or the sample-edge discontinuities. While suitable when $\varepsilon'$ is small, for the larger $\varepsilon'$ of biological materials a different approach is required.

Raj et al. (IEEE Trans. Instrum. Meas., Volume 50 (4), 905-909, August 2001) considered measuring liquids with a multilayered CPW configuration. To calibrate their sensor, as well as accounting for the sample-edge discontinuities, a set of calibration liquids with known $\varepsilon^*$ was measured, and empirical curve fitting was used. The empirically obtained curves are a function of the CPW dimensions and, therefore, new curves are needed for any change in dimension.

Huynen et al., (IEEE Trans. Instrum. Meas., Volume 50 (5), 1343-1348, October 2001) investigated the use of the multiline (Engen and Hoer, IEEE Trans. Microwave Theory Tech., Volume 27 (12), 897-903, December 1979; Marks, IEEE Trans. Microwave Theory Tech., Volume 39 (7), 1205-1215, July 1991) or line-line (Huynen et al, October 2001, supra) technique to measure the propagation constant of a microstrip line formed on a low-loss laminate substrate material. The multiline technique determines $\gamma$ by measuring two transmission lines that are identical, apart from a known length difference. This technique is therefore attractive for use with planar transmission lines, because $\gamma$ can be determined independent of any discontinuities. A numerical analysis (Huynen et al., October 2001, supra), based on a variational formulation (Huynen et al., IEEE Trans. Microwave Theory Tech., Volume 42 (11), 2099-2106, November 1994) was used to extract the substrate permittivity from the measured propagation constant. While the configuration (Huynen et al, October 2001, supra) is suitable for permittivity measurements of substrate materials, it is not mechanically suited to the measurement of materials placed on the planar line because considerable sample preparation is necessary to ensure that the two samples are identical, apart from a known length difference. In addition, the method adopted for the numerical extraction of the material permittivity requires significant computational resources.

The permittivity of a material is a function of its physical properties. Numerous techniques and configurations have been used to measure the permittivity of materials, as described above. For planar transmission-line sensors, there are several ways to extract $\varepsilon^*$ from the measured $\gamma$. One way is to use numerical techniques such as the spectral-domain technique (Huynen et al., 1994, supra) or the "method-of-moments" (Sonnet, www.sonnetsoftware.com). Numerical techniques, however, require considerable computational resources in order to obtain accurate results and therefore they are not particularly suited for rapid permittivity measurements in industrial settings. Another approach is to use analytic models that relate the line dimensions/parameters to $\gamma$ (Roelvink et al., 2013, supra; Stuchly and Bassey, 1998, supra; Raj et al., August 2001, supra). Such models can provide accurate results if the line dimensions/parameters are known. However, as demonstrated (Roelvink and Trabelsi, 2012 IEEE International Symposium on Antennas and Propagation and USNC-URSI National Radio Science Meeting, Chicago, Ill., 2012; herein incorporated by reference in its entirety), small dimensional uncertainties, particularly in regions where the fields are relatively concentrated, can result in large measurement uncertainty. This uncertainty increases as the dielectric constant C of the material increases (Roelvink and Trabelsi, Symposium and Meeting 2012, supra). If low-cost equipment is used to manufacture the planar transmission-line sensor, the dimensional uncertainty can be large. For such situations, an alternative approach for extracting $\varepsilon^*$ from $\gamma$ that does not require a precise knowledge of the line dimensions would be useful.

While various methods have been developed for measurement of properties of different materials, there remains a need in the art for a method for rapid, non-destructive, wideband permittivity measurements of materials such as liquids, powders, and semi-solid materials, especially those without uniform edges. There also remains a need in the art for a simple method for measuring the permittivity of materials with anisotropic properties. There also remains a need in the art for a simple calibration procedure for determining the material permittivity from the propagation constant measured with planar transmission lines. The present invention provides a simple two standard calibration technique and low-cost planar transmission-line sensor apparatus for rapid permittivity measurements on liquid, powders, and semisolid materials, which requires minimal sample preparation. It is also well suited for use in industrial environments as a sensor to determine moisture and density of powdered materials, quality parameters of food products such as meat, powdered foods, foods with a semi-solid consistency, and for characterization of biological materials to determine the physical properties of the material, such as the presence or absence of disease.

SUMMARY OF THE INVENTION

It is therefore an object of the present invention to provide a sensor apparatus, based on planar transmission lines, for rapid permittivity measurements for materials including materials without uniform edges, such as for example, liquid, powders, and semisolid materials with minimal sample preparation.

Another object of the present invention is to provide a calibration method that allows the direct determination of the material permittivity from the measured microwave scattering parameters with planar transmission lines.

A still further object of the present invention is to provide an accurate and simple method for the use of planar transmission lines to measure the anisotropic dielectric properties of materials that can be represented by a uniaxial permittivity tensor. Once the components of the permittivity tensor are determined, they can be used for rapid and nondestructive determination of physical properties of interest of foods, agricultural products and other biological and non-biological materials. Examples of applications include, but are not limited to, meat freshness, internal defects in agricultural products, presence of contaminants, and abnormalities in biological tissues. Examples of such materials are meat, timber and many wood products, some fruits, and other materials with a defined grain. These properties can be used to determine material parameters such as age or the difference between fresh and frozen food products.

Further objects and advantages of the present invention will be apparent from the following detailed description.

BRIEF DESCRIPTION OF THE DRAWINGS

FIG. 1 is a drawing of a sectional view of coplanar waveguide (CPW) transmission line showing relevant line parameters such as t, h, b, and a.

FIG. 2A is a top view including a long 16 and a short 14 planar transmission line, feed lines 20, substrate $\varepsilon_s$ 30, vias 22, and planar line lengths $l_1$ and $l_2$. FIG. 2B is a bottom view of apparatus 10 showing feed lines 20. FIG. 2C is a top view of apparatus 10 showing a sample holder 26 and liquid sample 28 sitting on substrate and over planar lines 14 and 16.

FIG. 7A shows $\varepsilon'$ dielectric constant on y axis and FIG. 7B shows $\varepsilon''$ dielectric loss factor on y-axis.

FIG. 8A shows $\varepsilon'$ dielectric constant on y axis and FIG. 8B shows $\varepsilon''$ dielectric loss factor on y-axis.

FIG. 9A shows $\varepsilon'$ dielectric constant on y axis and FIG. 9B shows $\varepsilon''$ dielectric loss factor on y-axis.

DETAILED DESCRIPTION OF THE INVENTION

Figure 1:
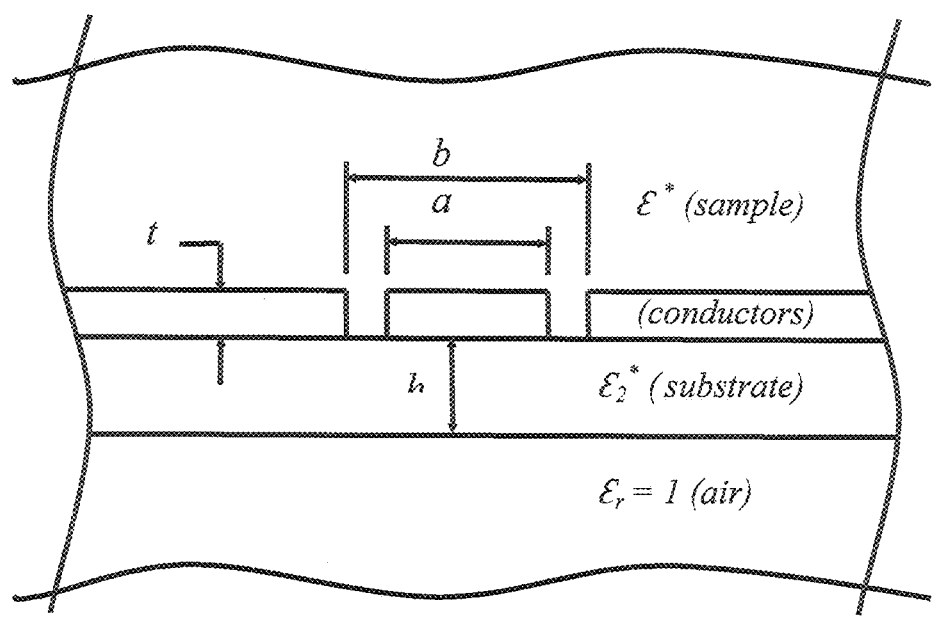

Dielectric methods are commonly used for rapid nondestructive measurement of attributes of products such as moisture content, fat content in agricultural products and food, lumber, chemical, pharmaceutical, concrete, and construction industries. The essence of dielectric methods is based on the electric field-material interaction which is characterized by the dielectric properties (complex permittivity). These properties can be highly correlated to the desired attributes of a material. The dielectric methods are useful because the electric field used by the sensing instruments penetrates materials well, providing volumetric sensing.

The present invention is a planar waveguide transmission-line sensor for measuring the wideband complex permittivity of liquids, powders, and semisolid materials such as biological materials at radiowave frequencies, microwave frequencies and millimeter-wave frequencies. Another aspect of the present invention is a new calibration method for planar waveguide transmission lines to provide a method for determining the material permittivity from the measured scattering parameters. A third aspect of the present invention is a method for measuring the dielectric anisotropy of materials with a defined grain, such as meat, wood, fruits, for example. The amount of anisotropy can be used to determine material parameters such as for example, tissue age, disease states of tissues, differences between fresh and frozen food products.

For planar transmission lines, the measured line propagation constant can be expressed as $$\gamma = \alpha + j\beta = \alpha_d + \alpha_r + \alpha_c + j\beta \quad (1)$$

where $j=\sqrt{-1}$, $\beta$ is the phase constant (rad/m) and $\alpha$ is the attenuation constant (np/m), which consists of $\alpha_d$, $\alpha_r$, $\alpha_c$; namely, the dielectric, radiation, and conductor attenuation constants, respectively (surface-wave losses are assumed to be negligible). All components in (1) are functions of the planar line dimensions, operating frequency, and material permittivity, $\varepsilon^*$. The problem can be separated into two parts: determination of $\gamma$ from scattering parameter measurements and determination of $\varepsilon^*$ from $\gamma$. The first object of this invention is to provide a calibration procedure for the direct determination of $\varepsilon^*$ from $\gamma$. This procedure is outlined in the following section. For clarity, it is first necessary to describe how $\gamma$ can be measured with planar transmission lines with the multiline or line-line technique (Janezic and Jargon, IEEE Microwave and Guided Wave Letters, Volume 9, 76-78, 1999). The second object of this invention is to provide a planar transmission-line sensor configuration for conveniently measuring the line propagation constant $\gamma$ with the multiline technique. This object is described in Section 2. The third object of the present invention is to provide a method for measuring the dielectric anisotropy of materials. This method is disclosed in Section 3.

Dielectric Calibration Method with Planar Transmission Lines

Determining $\gamma$

To determine the line propagation constant, $\gamma$, with the multiline technique (Janezic and Jargon, 1999, supra), two or more transmission lines are used that are identical, apart from a known length difference. The propagation constant $\gamma$ is calculated from uncalibrated scattering parameter measurements of each transmission line. The multiline expressions are for two transmission lines with a length difference $l_{\mathit{diff}} = l_2 - l_1$ are (Janezic and Jargon, 1999, supra):

$$\gamma = \frac{\ln(\lambda_{av})}{\ell_{\mathit{diff}}} + j\frac{2\pi n}{\ell_{\mathit{diff}}} \quad (2)$$

$$\lambda_{av} = \frac{1}{2}\left(\lambda_1 + \frac{1}{\lambda_2}\right) \quad (3)$$

$$\begin{pmatrix}\lambda_1 \\ \lambda_2\end{pmatrix} = \frac{M_{11} + M_{22} \pm \sqrt{(M_{11}+M_{22})^2 + 4M_{12}M_{21}}}{2} \quad (4)$$

$$M = T_{\ell 1}[T_{\ell 2}]^{-1} \quad (5)$$

$\lambda_1$ and $\lambda_2$ are the eigenvalues of matrix M, while $T_{\ell 1}$ and $T_{\ell 2}$ are the transmitting matrices for the transmission lines of length $l_1$ and $l_2$, respectively, which are obtained from the two-port scattering parameters (Janezic and Jargon, 1999, supra), measured with a appropriate hardware, such as for example a vector analyzer. If $l_{\mathit{diff}}$ is less than one-half wavelength, n=0 in (2). If $l_{\mathit{diff}}$ is more than one-half wavelength, n is an integer whose value can be obtained by comparing several possible solutions for $\beta$ at two frequencies (Roelvink et al., 2013, supra). An advantage of the multiline technique is that discontinuities on the transmission lines, such as those caused by the sample edges or sample holder, do not need to be modeled.

1.2 Determining $\varepsilon^*$ from $\gamma$

From transmission-line theory (Rizzi, *Microwave engineering: Passive Circuits,* 1988, New Jersey, USA: Prentice-Hall), the propagation constant due to the 'effective' complex relative permittivity of the material/line combination, $\varepsilon^*_{\mathit{eff}}$, is, $$\gamma_d = \alpha_d + j\beta = j\beta_0\sqrt{\varepsilon^*_{\mathit{eff}}} \quad (6)$$

where $\beta_0 = 2\pi f/c$ is the free-space phase constant (rad/m), f is the frequency (Hz) and $c = 2.99792 \times 10^8$ m/s is the speed of light in free space. $\varepsilon^*_{\mathit{eff}}$ is a function of the material and substrate permittivity, as well as the planar line dimensions and type. By way of an example, a cross section view of the CPW transmission line is given in FIG. 1, showing a coplanar waveguide transmission line with inner track width a, outer track width b, and conductor thickness t, feed lines and vias, substrate with permittivity $\varepsilon_s$ and height h. If the substrate permittivity and line dimensions are known, quasi-static analyses (Gupta et al., *Microstrip Lines and Slotlines,* 1979, Dedham: Artech House) or numerical techniques (Huynen et al., IEEE Trans. Microwave Theory Tech., Volume 42 (11), 2099-2106, 1994; Itoh and Mitra, IEEE Trans. Microwave Theory Tech., Volume 21, 496-499, 1973) can be used to obtain $\varepsilon^*_{\mathit{eff}}$ in terms of $\varepsilon^*$. However, the dimensional uncertainty can result in large measurement uncertainty (Roelvink and Trabelsi, 2013, supra). The present invention provides a calibration technique that does not require the substrate permittivity or the planar line dimensions to be known.

With the material placed in direct contact with the planar lines, the conformal mapping technique (Gupta et al., 1979, supra), or numerical techniques (Itoh and Mittra, 1973, supra), can be used to show that $\varepsilon^*_{\mathit{eff}}$ is a linear function of $\varepsilon^*$, namely, $$\varepsilon^*_{\mathit{eff}} = m\varepsilon^* + c^* \quad (7)$$

where the slope m is a scalar quantity that is a function of the planar line dimensions and is independent of frequency if the planar line dispersion is negligible. m approaches a value of 0.5 as the conductor thickness tends to zero (Roelvink and Trabelsi, 2013, supra; Gupta et al., 1979, supra). c* is a function of the planar line dimensions and the substrate permittivity, $\varepsilon^*_s$, which typically has some dielectric loss, and hence c* is a complex quantity. Equation (7) is appropriate for CPW, conductor-backed CPW, and two- or three-coplanar strips Gupta et al., 1979, supra).

If the combined radiation and conductor losses, $\alpha_r + \alpha_c$, are assumed to be negligibly small, two measurements of $\gamma$ for materials with known $\varepsilon^*$ are sufficient to determine m and c*. This was the approach reported in Roelvink and Trabelsi, IEEE International Instrumentation and Measurement Technology Conference (12MTC 2013); herein incorporated by reference in its entirety, where it was found that neglecting these losses resulted in significant error. In the present invention, rather than assuming $\alpha_r + \alpha_c = 0$, the losses are assumed to be of the form (Haydl et al., *Attenuation of millimeterwave coplanar lines on gallium arsenide and indium phosphide over the range 1-60 GHz,* In: *IEEE Int. Microwave Symp.,* Dig., 1992)

$$\alpha_r + \alpha_c \approx \alpha Re(\sqrt{\varepsilon^*}) \quad (8)$$

where Re(*) denotes the real part of * and a is a scalar, which is a function of the operating frequency, the substrate permittivity, and the planar line dimensions. Equation (8) was obtained from experimental measurements of CPW on low-loss dielectric substrates over a large range of microwave frequencies (Haydl et al., 1992, supra; Ponchak et al., IEEE Trans. Microwave Theory Tech., Volume 47, 241-243, 1999) and is more appropriate than the form obtained with the closed-form expressions used in (Roelvink, et al, 2013, supra). To determine the constants in (7) and (8), three measurements of γ with known ε* can be made. However, some simplification is possible: By recognizing that, for high-loss materials $\alpha_d \gg \alpha_r + \alpha_c$, while for low-loss materials a $Re(\sqrt{\varepsilon^*}) \approx a(\sqrt{\varepsilon^*})$, (6)-(8) can be substituted into (1) and, after some simplification, $$\varepsilon^* = \frac{1}{d^*}\left[\left(\frac{\gamma}{\beta_0}\right)^2 + c^*\right] \quad (9)$$

where $d^* \approx m - j2\alpha\sqrt{m}/\beta_0$. The imaginary part of d* accounts approximately for the effect of the conductor and radiation losses, which are often significant, particularly for calculating ε". Equation (9) is an equation of a straight line with slope $-1/d^*$ and intercept $-c^*/d^*$. The two complex quantities can be obtained from two measurements of γ for materials with known ε*, namely, $$d^* = \frac{\gamma_1^2 - \gamma_2^2}{\beta_0^2(\varepsilon_1^* - \varepsilon_2^*)} \quad (10)$$

$$c^* = \left(\frac{\gamma_1}{\beta_0}\right)^2 - d^*\varepsilon_1^* \quad (11)$$

where the subscripts refer to each measured material. Natural choices for the calibration standards are air, ε*=1, and a reference liquid, such as distilled water (Kaatze, Meas. Sci. Technol., Volume 18, 967-976, 2007) and it is found that these standards give relatively small measurement uncertainty (Roelvink et al, Meas., Sci. Technol., Volume 24, 1-8, 2013; herein incorporated by reference in its entirety). This simple calibration procedure yields very accurate results for a large range of microwave frequencies and materials. An example of how this technique can be applied is given in Example 1.

2. Planar Transmission-line Sensor Apparatus

The planar transmission-line sensor apparatus 10 shown in FIGS. 1-4 includes a metal-clad substrate 30, short planar transmission line 14, long planar transmission line 16, board top side 18, board bottom side 19, feed lines 20, plated through-hole via 22, microstrip-to-coaxial line transition 24, and sample holder 26 if needed for liquid samples.

Figure 2A:
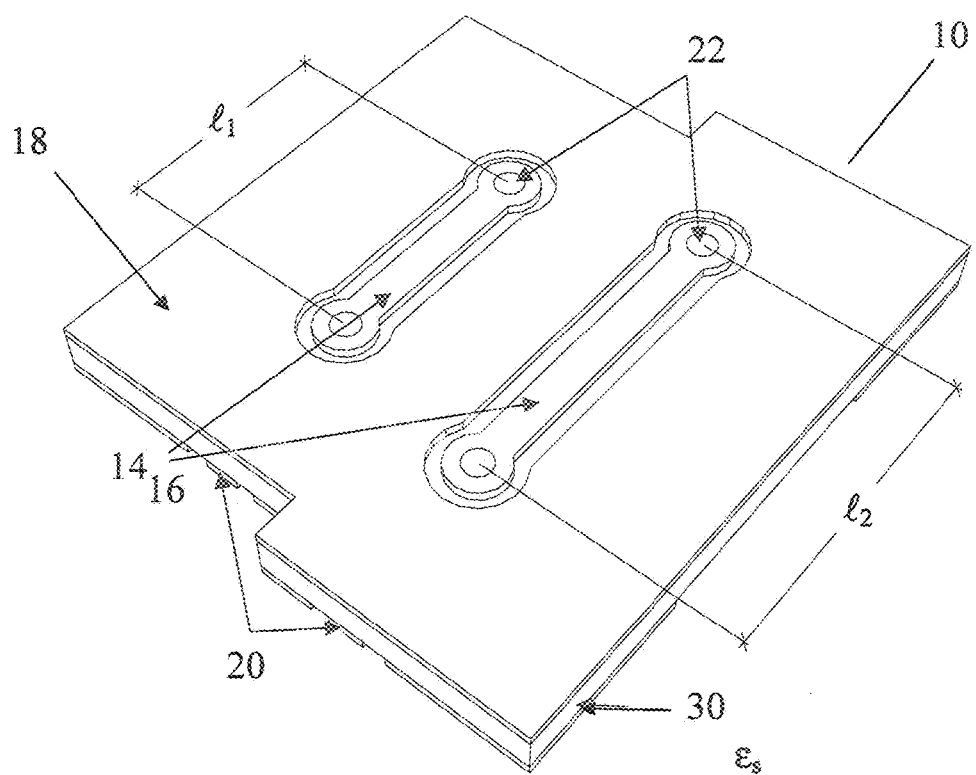
FIGS. 2A-2C are drawings showing three views of planar transmission-line-sensor apparatus 10.
Figure 2B:
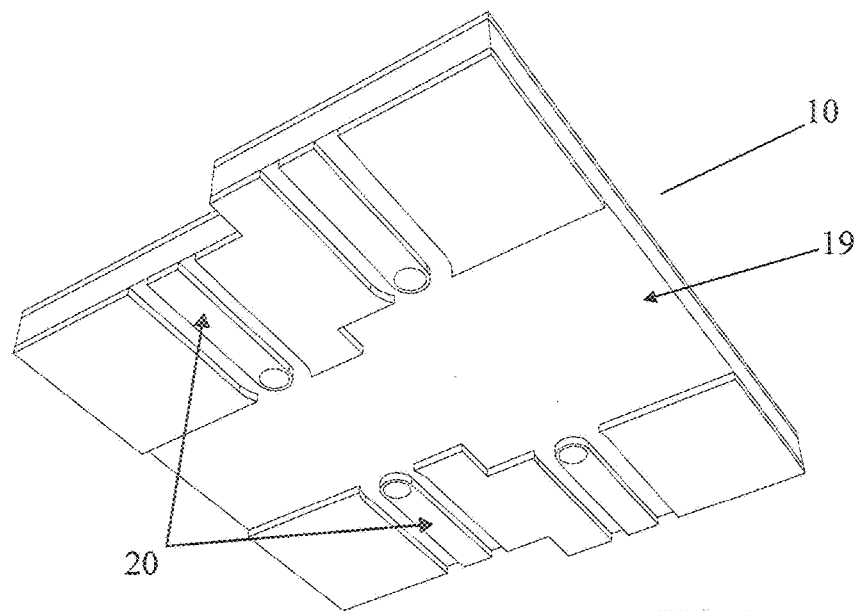
Figure 2C:
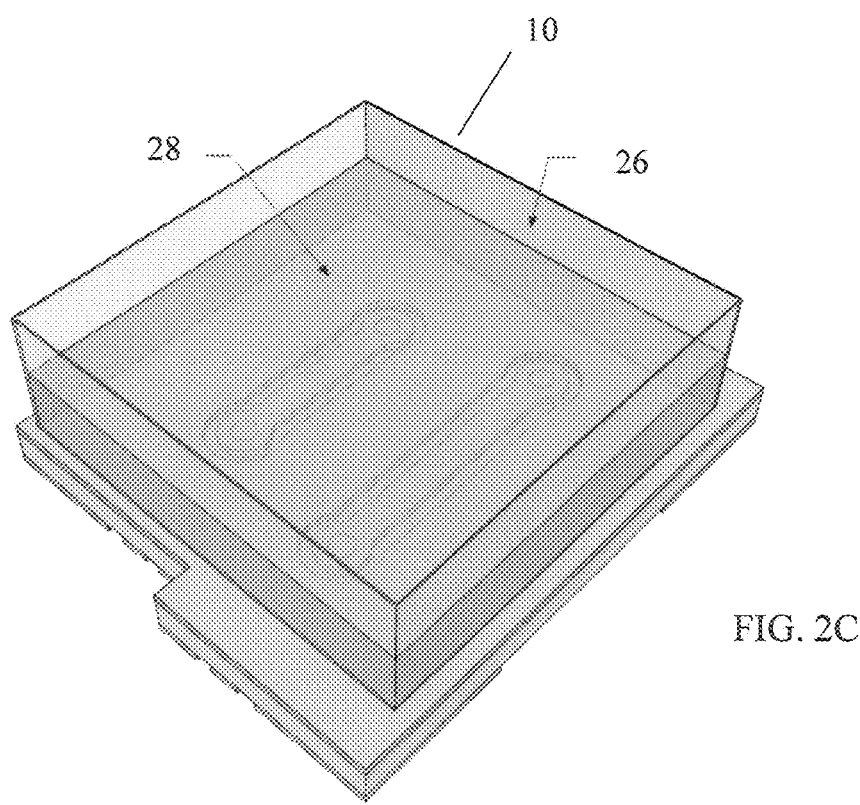

The multiline technique for determining γ can be used with transmission lines 14 and 16 that contain discontinuities, such as those introduced by the plated through-hole vias 22 connecting the board bottom side and the board top side, the only requirement being that the two lines 14 and 16 are identical except for the known length difference $l_{diff}$. This removes the need to explicitly model the effect of the discontinuities. FIG. 2 depicts an example of a transmission-line arrangement. FIG. 2 shows an arrangement made on a double-sided printed circuit board, with planar transmission lines 14 and 16 etched or milled on the board top side 18 (FIG. 2(A)) and connected to two feed lines 20 which are etched or milled on the board bottom side 19 (FIG. 2(B)) by a means for connecting transmission lines such as, for example, plated through-hole via 22, metal post (not shown) or other connections such as tab inter-connects, or inductively-coupled transitions. The advantage of this arrangement is that as long as the sample material has a flat face that completely covers the two planar lines, the sample edges are removed from the planar line fields. Hence, this arrangement can be used to measure materials with irregular edges, such as semisolid biological materials. If a sample holder 26 is required in the case of liquid samples 28, it can be positioned away from the planar lines 14 and 16 where it will not affect the measurement as shown in FIG. 2(C). To minimize the impedance mismatch, the feed-line 20 and planar-line 14 and 16 dimensions are chosen to have a characteristic impedance of approximately 50Ω. For the planar line, these dimensions are selected with the expected dielectric constant of the sample material in place.

The error in γ calculated with equation 2, due to linear errors in the eigenvalues, decreases as the line length difference, $l_{diff}$, increases (Marks, IEEE Trans. Microwave Theory Tech., Volume 39 (7), 1205-1215, 1991). However, if one of the lines is made too long, the transmitted signal will be comparable to the noise floor of the measurement instrument, which can result in significant measurement error. To provide a simple method for selecting the appropriate length of the longest line 16, an approximate expression for the line length in terms of the maximum permissible linear attenuation $A_{max}$ is:

$$\ell_{max} \approx -\frac{\ln(A_{max}/1 - |\rho|^2)}{Re(j\beta_0\sqrt{\varepsilon_{eff}^*})} \quad (12)$$

where Re(*) denotes the real part of *, and ρ is the reflection coefficient due to the transition between the feed line and the sample-covered planar transmission line, which can be approximated as:

$$\rho \approx \frac{\sqrt{\varepsilon_{eff}^U} - \sqrt{\varepsilon_{eff}^*}}{\sqrt{\varepsilon_{eff}^U} + \sqrt{\varepsilon_{eff}^*}} \quad (13)$$

Where $\varepsilon_{eff}^U$ effective permittivity of the feed line, which can be estimated by using a closed-form expression (Gupta et al., Microstrip Lines and Slotlines, 1979, Dedham: Artech House). $\varepsilon^*_{eff}$ can be obtained from (7) by using typical approximate values for d* and c* such as 0.5 and 2 respectively and the expected range of ε* for the material to be measured.

Figure 4:
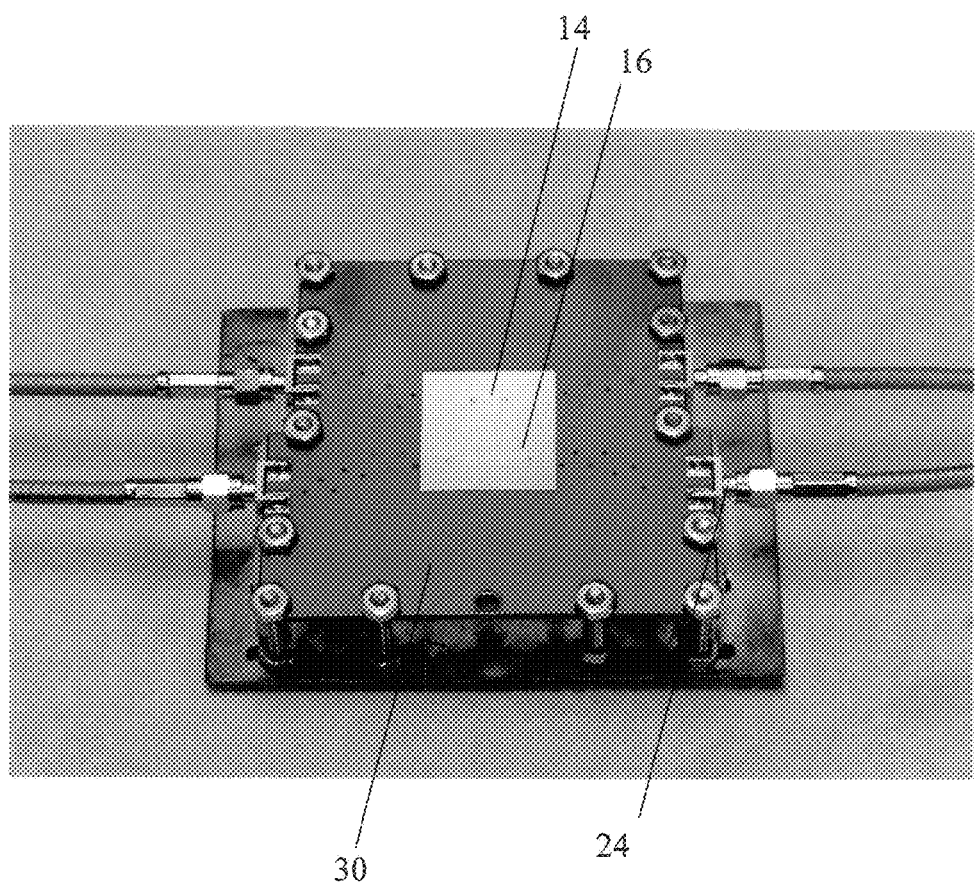
FIG. 4 is a photograph of a CPW sensor 10 showing CPW planar lines 14 and 16, substrate 30, and microstrip-to-coaxial line transitions 24.

An example of how this sensor can be used in conjunction with the calibration procedure (described in Section 1) is given in Example 1. FIG. 4 shows a photo of the sensor apparatus used in Example 1 and described in this section. FIG. 4 shows hard-gold plated CPW lines 14 and 16 that were manufactured on an FR4 laminate substrate 30. The line length difference, $l_{diff}$, was 10 mm. The CPW lines 14 and 16 were approximately 9-mm and 19-mm and were connected to microstrip feed lines on the underside of the board by metal post connections. Microstrip-to-coaxial line transitions 24 were used on each of the feed lines.

For these dimensions, the characteristic impedance of the feed lines is approximately 50Ω, The CPW line is approximately 50Ω when ε'=10 The approximately 19-mm line was chosen by using equation (12), with $A_{max}$=0.032 (about (30 dB)), ε*=53−j27 which is approximately the permittivity of a 25/75% ethanol/water mixture at approximately f=5 GHz.

3. Anisotropy Measurement Technique

Figure 3A:
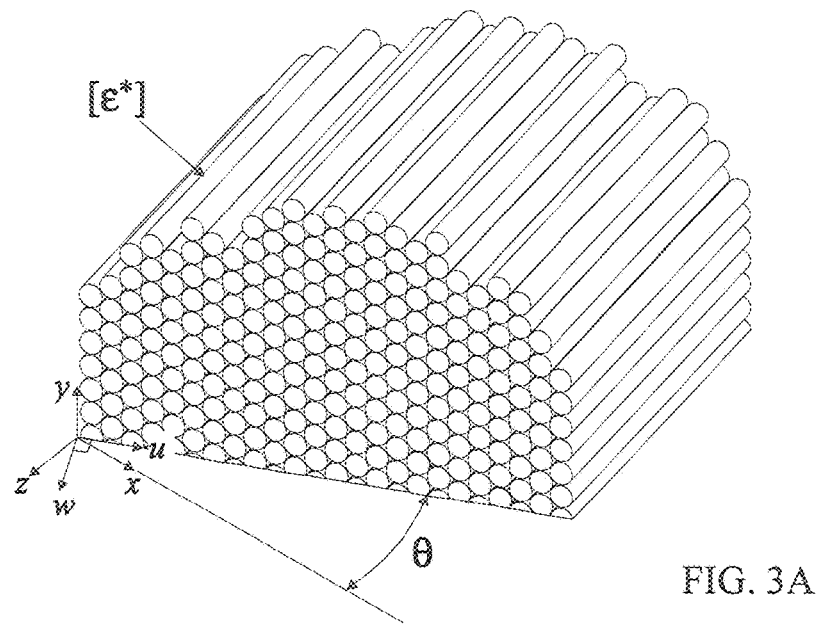
FIG. 3A is a drawing of a material having a uniaxial permittivity tensor. Materials with a grain such as wood and muscle tissue can be represented by a uniaxial permittivity tensor. Cartesian coordinate system are shown relative to the sensor (x,y,z) and the material (u,y,w).

A material with a uniaxial permittivity is shown FIG. 3A. The Cartesian coordinate systems associated with the planar sensor apparatus and the material are (x,y,z) and (u,y,w), respectively, where u and w are x and z are rotated by $\theta$ radians about the y axis. The relative complex permittivity tensor of the material, with respect to (x,y,z), is, $$[\varepsilon^*] = [\varepsilon' - j\varepsilon''] = \begin{bmatrix} \varepsilon_\perp^* \cos^2\theta + \varepsilon_\parallel^* \sin^2\theta & 0 & (\varepsilon_\perp^* - \varepsilon_\parallel^*)\sin\theta\cos\theta \\ 0 & \varepsilon_\perp^* & 0 \\ (\varepsilon_\perp^* - \varepsilon_\parallel^*)\sin\theta\cos\theta & 0 & \varepsilon_\perp^* \sin^2\theta + \varepsilon_\parallel^* \cos^2\theta \end{bmatrix} \quad (14)$$

where $\varepsilon^*_\perp = \varepsilon'_\perp - j\varepsilon''_\perp$ and $\varepsilon^*_\parallel = \varepsilon'_\parallel - j\varepsilon''_\parallel$ are the perpendicular and parallel components of the permittivity tensor and $j=\sqrt{-1}$.

Figure 3B:
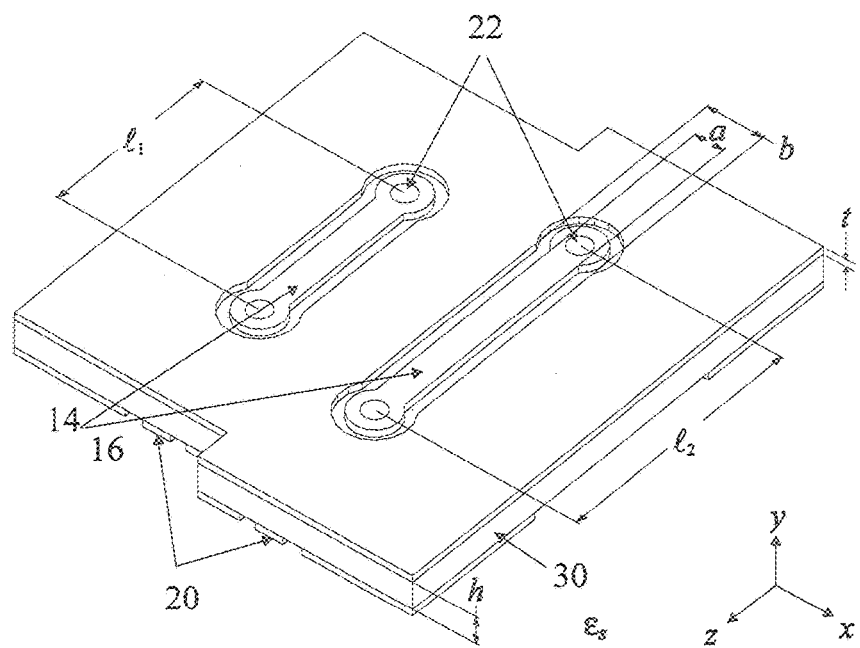
FIG. 3B is a drawing showing coplanar lines 14 and 16 with inner track width a, outer track width b, and conductor thickness t, feed lines 20 and vias 22, substrate 30 with permittivity $\varepsilon_s$ and height h. The planar line lengths are $l_1$ and $l_2$.

With equation (9) the relative permittivity measured with the CPW configuration in FIG. 3B can be expressed as, $$\varepsilon^*_{meas}(\theta) = \varepsilon'_{meas}(\theta) - j\varepsilon''_{meas}(\theta) = -\frac{1}{d^*}\left[\left(\frac{\gamma(\theta)}{\beta_0}\right)^2 + c^*\right] \quad (15)$$

where $\gamma(\theta)$ is determined from (2), and d* and c* are determined from equations (10) and (11) respectively.

For uniaxial materials, referenced to (x,y,z), $\varepsilon^*_{meas}(\theta)$ is a function of the sample orientation, namely (Torgovnikov, 1993, supra), $$\varepsilon^*_{meas}(\theta) = \varepsilon^*_u \cos^2\theta + \varepsilon^*_w \sin^2\theta \quad (16)$$

where $\varepsilon^*_u = \varepsilon'_u - j\varepsilon''_u$ and $\varepsilon^*_w = \varepsilon'_w - j\varepsilon''_w$ represent the measured permittivity with respect to the sample axes. For uniaxial materials oriented as in FIG. 3A, $\varepsilon^*_u = \varepsilon^*_\perp$. The determination of $\varepsilon^*_w$ is less obvious. It was found (Kitazawa and Hayashi, IEEE Trans. Microwave Theory Tech., Volume 29, 1035-1037, 1981; Kobayashi and Terakado, IEEE Trans. Microwave Tech., Volume 27, 769-778, 1979) that, as the conductor thickness, t, of the CPW lines approaches zero, $\varepsilon^*_w = \sqrt{\varepsilon^*_\perp \varepsilon^*_\parallel}$. In practice however, t≠0, which results in a larger proportion of x-directed electric field. $\varepsilon^*_w$ is therefore more influenced by $\varepsilon^*_\parallel$ than when t=0. The error in $\varepsilon^*_w$ predicted with the t=0 expression can be large for materials with considerable anisotropy. To account approximately for the effect of t, we have obtained a simple empirically derived correction to the t=0 result, namely, $$\varepsilon^*_w = \sqrt{\varepsilon^*_\perp \varepsilon^*_\parallel} + (\varepsilon^*_\parallel - \varepsilon^*_\perp)(d^*/d^0 - 1) \quad (17)$$

where $d^0$ is the calibration constant for t=0 and the ratio $d^*/d^0$ directly accounts for the effect of t, in a manner similar to the empirically derived correction presented in (Gupta et al., 1979, supra, p. 278). When $\varepsilon^*_\perp = \varepsilon^*_\parallel$ or $d^* = d^0$, $\varepsilon^*_w$ reduces to $\sqrt{\varepsilon^*_\perp \varepsilon^*_\parallel}$. For CPW, $d^0 = 0.5$ (Gupta, et al., 1979, supra; Roelvink et al, 2013 supra). For conductor-backed CPW (Gupta et al., 1979, supra), $$d^0 = \left[1 + \frac{K'(a/b)K(\tanh(\pi a/4h)/\tanh(\pi b/4h))}{K(a/b)K'(\tanh(\pi a/4h)/\tanh(\pi b/4h))}\right]^{-1} \quad (18)$$

where K(*) is the complete elliptic integral and $K'(*) = K(\sqrt{1-(*)^2})$. Accurate approximations for K(*)/K'(*) have been derived (Hillberg, IEEE Trans. Microwave Theory Tech., Volume 17, 259-269, 1969). Equation (18) approaches 0.5 as the ratio b/h is decreased.

From (16), the geometric interpretation of $1/\sqrt{\varepsilon'_{meas}(\theta)}$ and $1/\sqrt{\varepsilon''_{meas}(\theta)}$ are ellipses with $\sqrt{\varepsilon'_u}$ and $\sqrt{\varepsilon''_u}$, and $\sqrt{\varepsilon'_w}$ and $\sqrt{\varepsilon''_w}$ as the semimajor and semiminor axes respectively. This provides a convenient and numerically efficient measurement-based method for determining $\varepsilon^*_\perp$ and $\varepsilon^*_\parallel$ from $\varepsilon^*_{meas}(\theta)$: 1. The permittivity of the sample material is measured for a range of known $\theta$ ... 2. The inverse square roots of $\varepsilon'_{meas}(\theta)$ and $\varepsilon''_{meas}(\theta)$ are fitted with ellipses by a direct least squares fitting algorithm (Fizgibbon et al., IEEE Trans. Pattern Analysis and Machine Intelligence, Volume 21, 476-480, 1999) without recourse to iterative numerical fitting procedures. 3. $*\varepsilon_\perp$ and $\varepsilon^*_\parallel$ are extracted from the coefficients of the fitted ellipses. This method removes the need to measure carefully prepared and aligned samples (Akhtar et al., IEEE Trans. Microwave Theory Tech., Volume 54, 2011-2022, 2006; Torgovnikov, Dielectric properties of wood and wood-based materials. Wood science, ed. T. E. Timell, 1993, Berlin: Springer-Verlag). Instead, relatively easily prepared and nonaligned samples are measured at a number of known angles, $\theta$. Increasing the number of measured angles increases the accuracy of the inferred $\varepsilon^*_\perp$ and $\varepsilon^*_\parallel$. Examples of how this technique can be applied are given in Example 2.

In addition to the practical applications of the present invention described above, a further application is in the construction of models for the dielectric heating of materials such as in industrial microwave or radio frequency heating equipment. Such arrangements can be modeled by using analytical field theory (Rizzi, Microwave engineering: Passive circuits; 1988; New Jersey, USA; Prentice Hall) or with numerical techniques (COMSOL Multiphysics www.comsol.com), and require the accurate knowledge of the permittivity of the material to be heated. The present invention discloses an accurate and efficient technique and apparatus for measuring the permittivity of many such materials.

The following examples are presented to illustrate the use of the present invention for measuring the permittivity of a material sample. Cyclohexane, ethanol, and various aqueous solutions of ethanol, chicken and beef, and gelatin and sawdust are used as test models in the present invention. The examples are intended to illustrate the invention and are not intended to limit the scope of the defined claims.

EXAMPLE 1

Permittivity Measurements on Liquids

Figure 5:
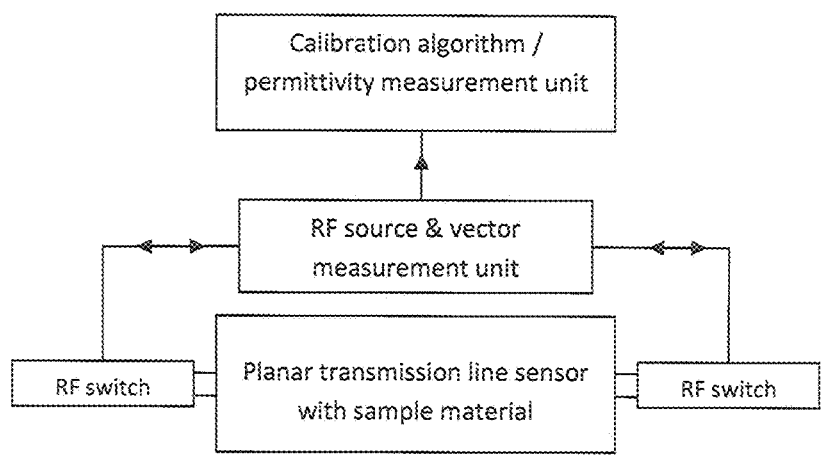
FIG. 5 is a block diagram of the planar transmission line sensor and associated measurement hardware.

This example demonstrates how to measure the permittivity of liquids with the present invention. The scattering parameters were obtained for three aqueous solutions of ethanol and three reference liquids placed on the CPW lines over the frequency range 0.5-5 GHz with an Agilent E5071C ENA series network analyzer connected to each of the coaxial connectors as shown in FIG. 5. The scattering parameters without any sample present, $\varepsilon^* = 1$, were also measured. The aqueous solutions of ethanol (purity ≥99.5%) were mixed by mass with distilled water. Permittivity results were then calculated by using the technique described in Section 1. The permittivity results were compared to measurements obtained with an Agilent 85070B coaxial-line probe and reference data for each liquid (Kaatze, 2007, supra; Green, *Measurements of the dielectric relaxation spectra of nine liquids and binary mixtures at 20° C. and microwave frequencies*, in Proceedings of the Conference on Precision Electromagnetic Measurements, 212-213, 1996). All measurements were made at 20 degrees C.

FIG. 4 shows a photo of hard-gold plated CPW lines 14 and 16 that were manufactured on an FR4 laminate substrate 30. The line length difference, $l_{diff}$, was approximately 10 mm. The CPW lines 14 and 16 were connected to micro strip feed lines 20 on the underside of the board by metal post 24 connections. The microstrip-to-coaxial line transitions 32 were used on each of the feed lines. This forms the sensor apparatus as described in section 2.

Figure 6A:
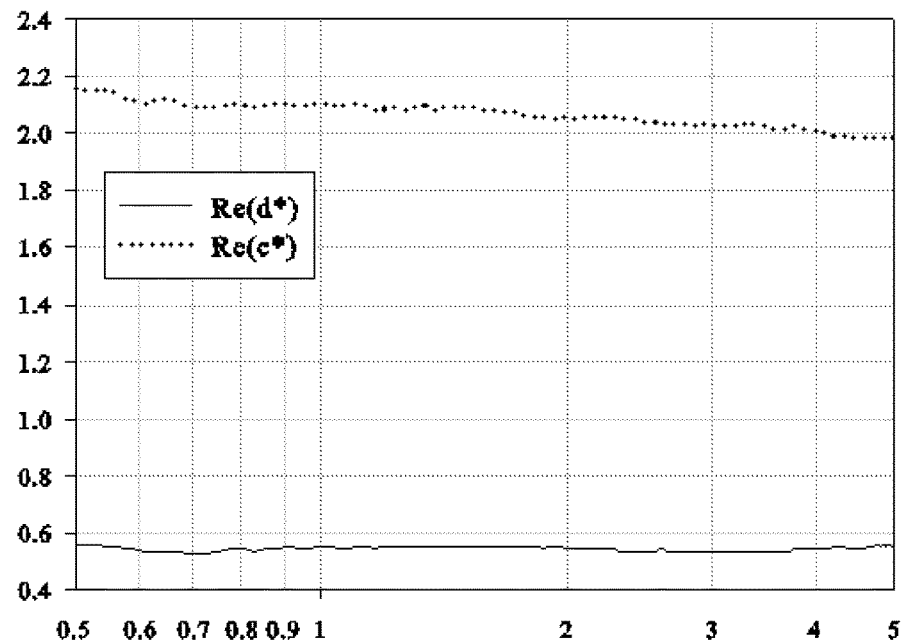
FIGS. 6A and 6B are graphs showing the calibration constants d* and c* as a function of frequency, calculated with calibration standards of $\varepsilon^*_1=1$ (air) and distilled water for $\varepsilon^*_2$. The real parts of d* and c* are shown in FIG. 6A and the imaginary parts of d* and c* are shown in FIG. 6B.
Figure 6B:
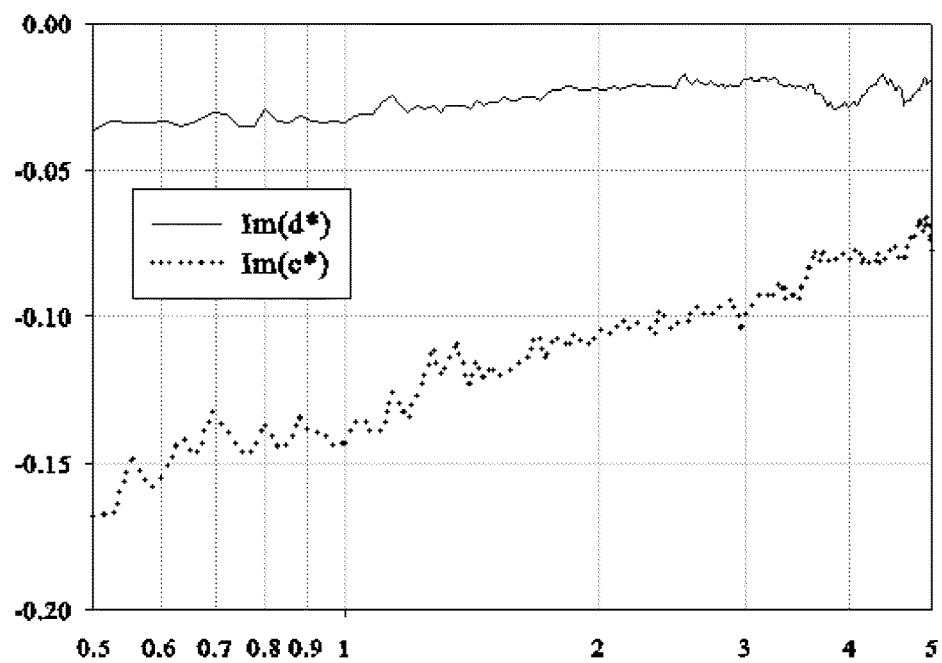

Results are presented in FIG. 6 for the calibration constants d* and c* calculated from γ measurements with air, $\varepsilon^*_1=1$, and distilled water for $\varepsilon^*_2$ (Kaatze, 2007, supra). The real part of d* is close to 0.5, as expected for CPW, and essentially constant with frequency, indicating that dispersion effects of the lines over this frequency range are small.

Figure 7A:
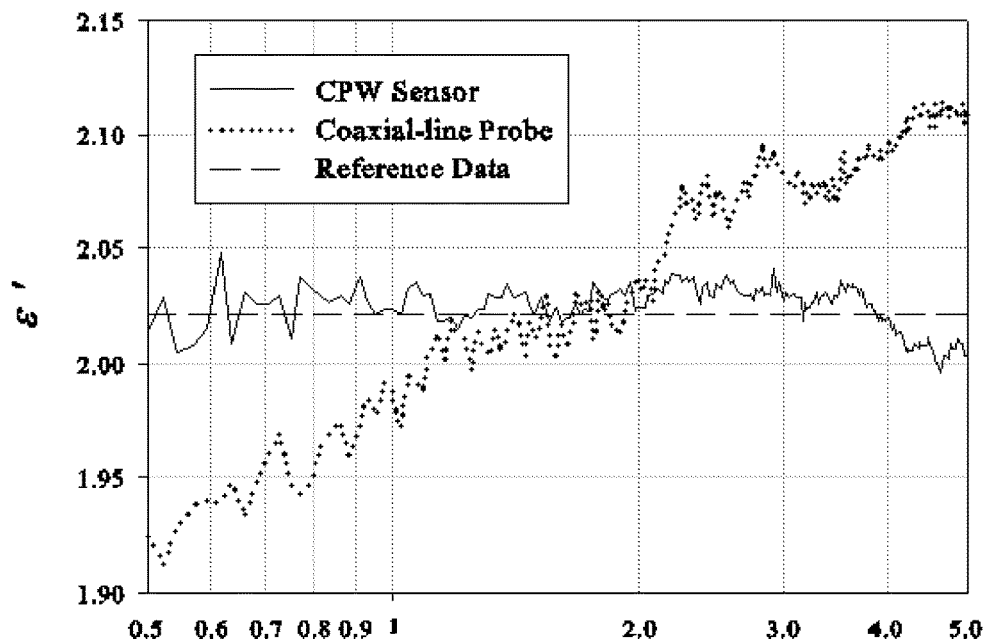
FIGS. 7A and 7B are graphs comparing results for $\varepsilon^*$ as a function of frequency for cyclohexane.
Figure 7B:
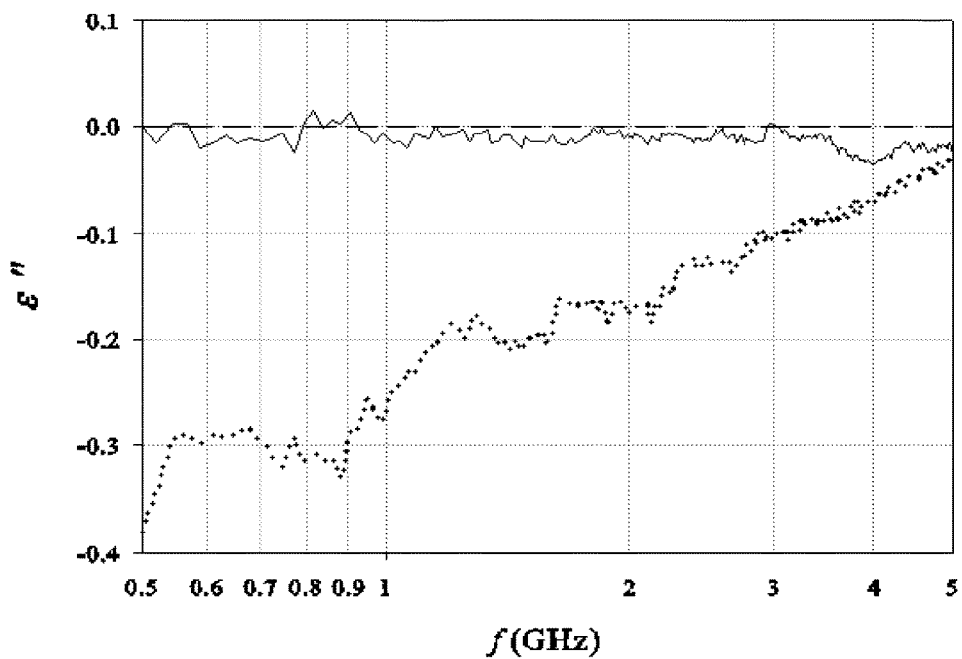
Figure 8A:
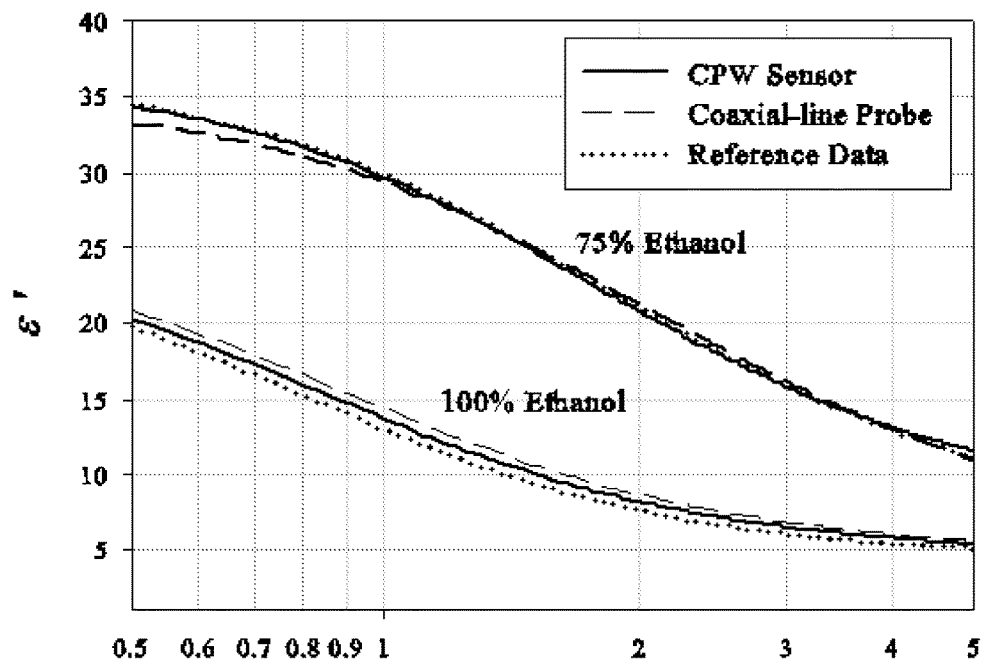
FIGS. 8A and 8B are graphs comparing results for $\varepsilon^*$ as a function of frequency for ethanol and 75/25% ethanol/water mixture at 20 degrees C.
Figure 8B:
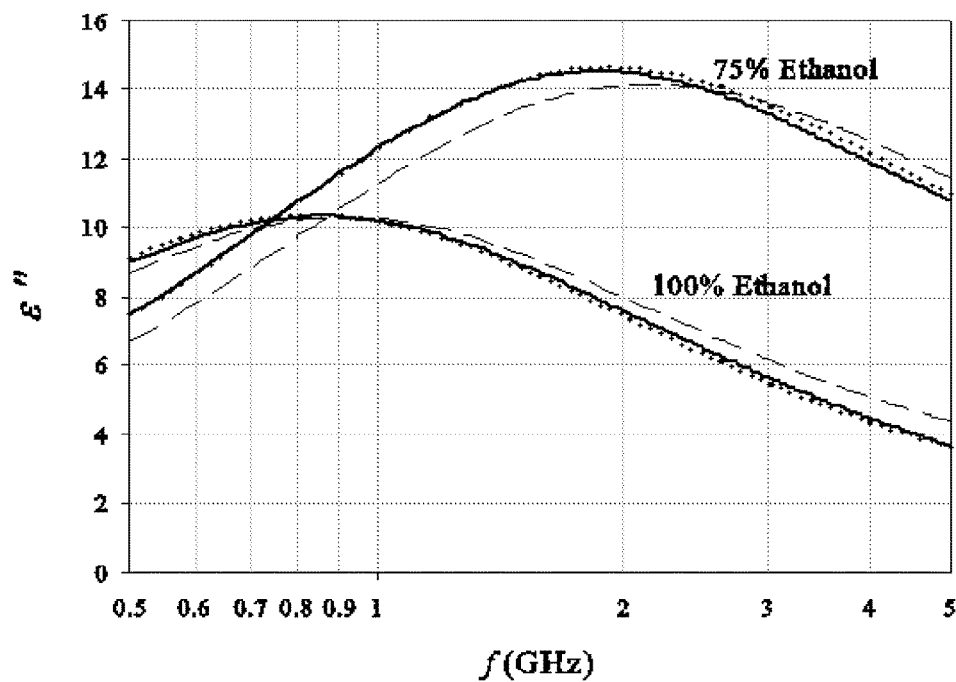
Figure 9A:
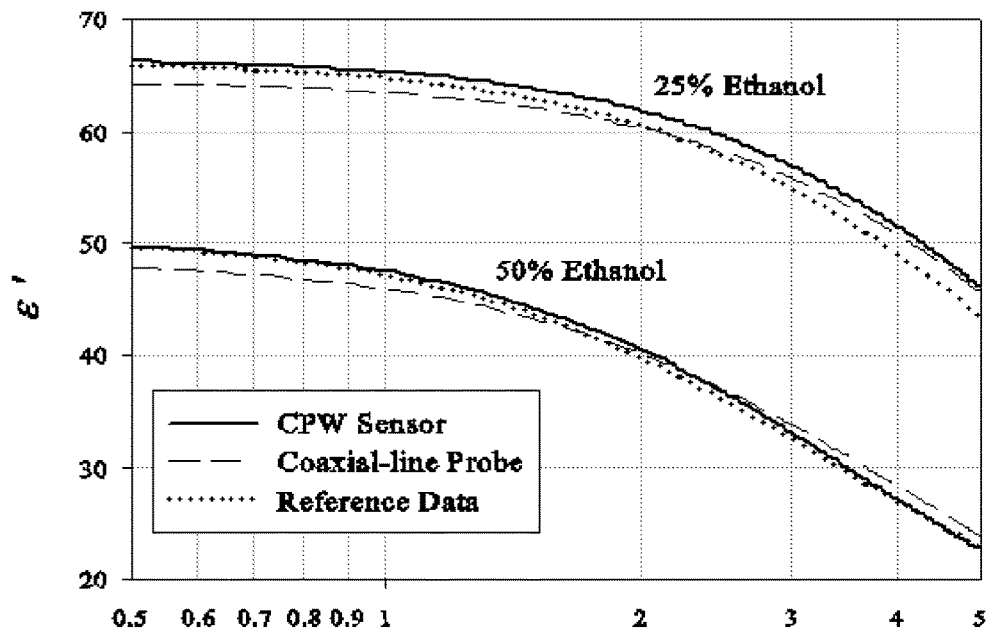
FIGS. 9A and 9B are graphs comparing results for $\varepsilon^*$ as a function of frequency for 50/50% and 25/75% ethanol/water mixtures at 20 degrees C.
Figure 9B:
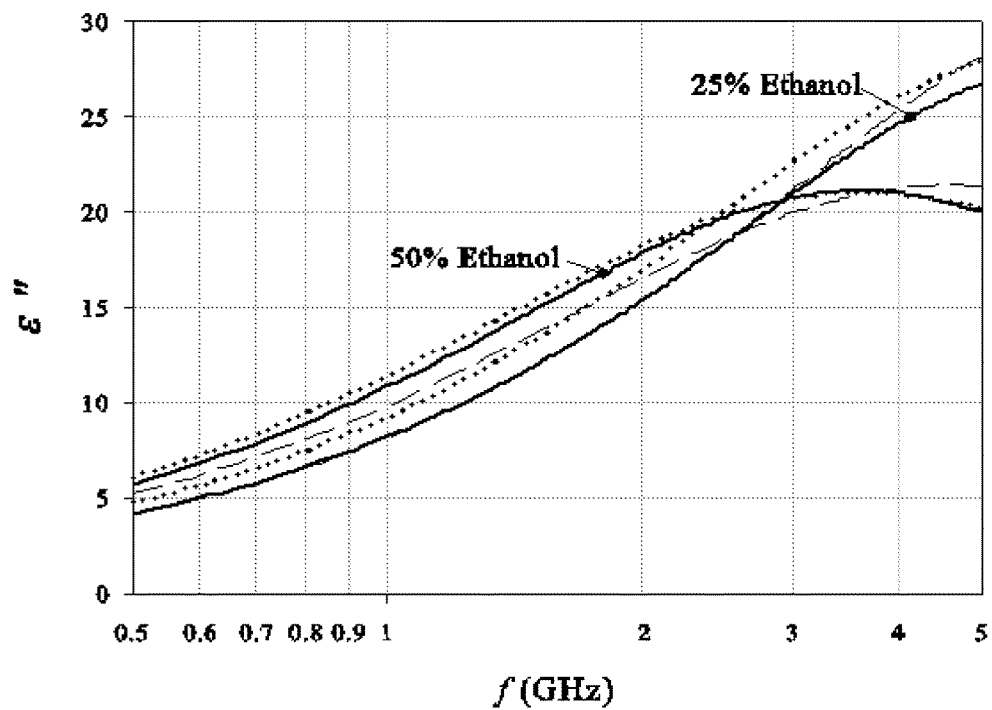

FIG. 7 shows results for ε* for cyclohexane, a low-permittivity reference liquid that is nondispersive and lossless (Kaatze, 2007, supra). The agreement between the CPW sensor and the reference data is very good with a maximum relative difference of 1%, while the coaxial-line probe measurement has a larger error (maximum relative error of 5%). FIGS. 8 and 9 show results for ε* for pure ethanol and three aqueous solutions of ethanol. All results have been fitted with appropriate Debye models (Green, 1996, supra; Gregory and Clarke, NPL Report, MAT 23, National Physical Laboratory, 2009). The CPW results are in excellent agreement with the reference data, with maximum relative errors of 5%, 1%, 1% and 3%; for ethanol, 75/25%, 50/50% and 25/75% ethanol/water mixtures, respectively. The maximum relative errors of the coaxial-line probe measurements were larger in all cases; 13%, 4%, 5% and 4%, respectively. The larger error in the measurements made with the commercial coaxial-line probe can be explained by the probe-aperture model, which contains terms that are measured once by the manufacturer for a given probe, and are not corrected during subsequent calibrations (Blackham and Pollard, IEEE Trans. Instr. Meas., Volume 46, 1093-1099, 1997). Therefore, the calibration procedure for the commercial coaxial-line probe does not fully account for changes in the probe-aperture dimensions over time, which can be due to mechanical and thermal stresses. The method of calibration disclosed here does not suffer from this limitation.

This example demonstrates that very accurate measurements of the permittivity of materials can be made by using both the calibration technique and the planar transmission-line sensor apparatus described herein.

EXAMPLE 2

Anisotropy Measurements on Biological Materials

Because of the difficulty in producing samples with known anisotropic dielectric properties, the anisotropy measurement technique (Section 3) is first demonstrated by using numerical simulation software (COMSOL Multiphysics www.comsol.com). The two-port scattering parameters of two lengths, 20- and 30-mm, of material-loaded conductor-backed CPW transmission line 14 and 16 at 2 GHz were obtained from simulations. The propagation constant, γ(θ), was obtained from the simulated scattering parameters by using the multiline technique.

The calibration constants in (15) were first obtained from simulations of two materials with known homogeneous ε* (Roelvink et al, 2013, supra). Several combinations of $\varepsilon^*_\perp$ and $\varepsilon^*_\parallel$ were considered and for each combination θ was varied from zero to π/2 in π/24 steps (one quadrant was sufficient due to symmetry). The samples were orientated as shown in FIG. 3. Note, however, that the technique described in Section 3 can be used with materials that have different, and unknown, starting angles. The CPW parameters in FIG. 1 were; a=0.4 mm, b=0.8 mm, h=1.6 mm, t=35 μm, and $\varepsilon_s$=4. From the calibration procedure (Roelvink et al, 2013, supra) d*=0.546 and c*=1.81. (d* and c* are real since the simulated radiation and conductor losses were negligible Roelvink et al, 2013, supra). From (18), $d^0$=0.495.

TABLE I

COMPARISON OF THE MODELLED AND EXTRACTED PERMITTIVITY AT 2 GHz

| Modelled | | Extracted | | Error (%) | |
|---|---|---|---|---|---|
| $\varepsilon_\perp^*$ | $\varepsilon_\parallel^*$ | $\varepsilon_\perp^*$ | $\varepsilon_\parallel^*$ | $|\varepsilon_\perp^*|$ | $|\varepsilon_\parallel^*|$ |
| 9 − j1.9 | 27 − j6.8 | 9.1 − j1.92 | 27.8 − j7.07 | 1.61 | 3.00 |
| 30 − j8 | 35 − j10 | 29.9 − j8.0 | 35.9 − j10.0 | 0.24 | 0.40 |
| 35 − j10 | 45 − j15 | 34.9 − j10.0 | 44.7 − j15.0 | 0.41 | 0.60 |
| 57 − j14 | 60 − j15 | 56.8 − j14.1 | 59.7 − j15.0 | 0.39 | 0.45 |

TABLE II

MEASURED PERMITTIVITY TENSOR FOR SEVERAL MEAT SAMPLES AT 2.45 GHz ($r^2$ VALUES ARE FOR THE FITTED ELLIPSES)

| Sample | $\varepsilon_\perp^*$ | $\varepsilon_\parallel^*$ | $r^2(1/\sqrt{\varepsilon'})$ | $r^2(1/\sqrt{\varepsilon''})$ |
|---|---|---|---|---|
| Chicken 1 | 55.9 − j19.4 | 58.5 − j20.6 | 0.97 | 0.97 |
| Chicken 2 | 53.4 − j18.5 | 62.0 − j20.5 | 0.89 | 0.93 |
| Chicken 3 | 57.5 − j19.4 | 61.4 − j21.0 | 0.99 | 0.99 |
| Chicken 4 | 50.0 − j16.6 | 61.9 − j20.3 | 0.94 | 0.95 |
| Beef 1 | 49.0 − j15.2 | 59.2 − j18.8 | 0.88 | 0.89 |

Figure 10:
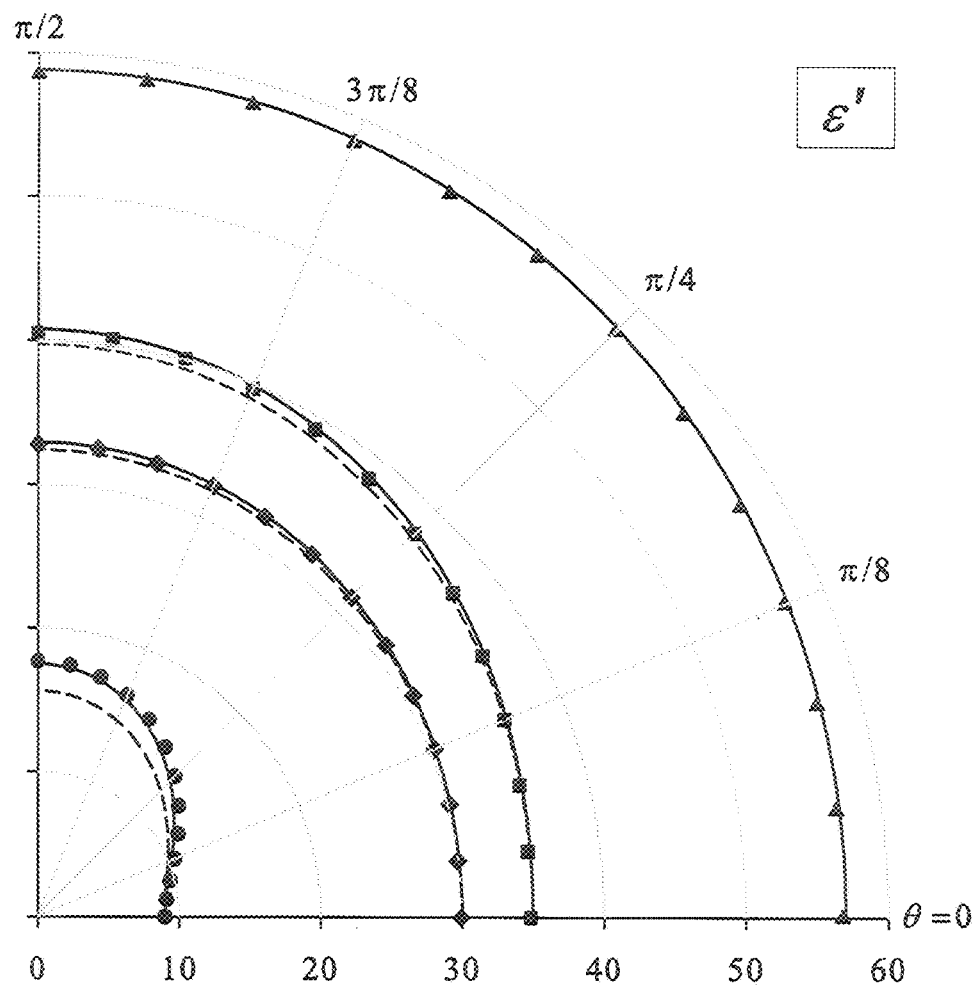
FIG. 10 is a graph showing results calculated from simulations compared to those predicted with $\varepsilon^*_{meas}(\theta)=\varepsilon^*_u \cos^2\theta + \varepsilon^*_w \sin^2\theta$ at 2 GHz.

FIG. 10 compares results for $\varepsilon'_{meas}(\theta)$, obtained from the simulated scattering parameters and (15), to results calculated with (16), for several different materials. (Note $\varepsilon''_{meas}(\theta)$ is not shown for brevity.) Clearly, (16) accurately represents the form of $\varepsilon^*_{meas}(\theta)$. Also included in this figure is the t=0 theoretical result for the lowest three permittivity samples. The appreciable difference between the results demonstrates the need to correct for the conductor thickness. Table I compares permittivity tensor results extracted from the fitted elliptical coefficients of $1/\sqrt{\varepsilon'_{meas}(\theta)}$ and $1/\sqrt{\varepsilon''_{meas}(\theta)}$ (obtained with the direct least squares fitting algorithm (Fizgibbon et al., IEEE Trans. Pattern Analysis and Machine Intelligence, Volume 21, 476-480, 1999)) to the modeled $\varepsilon^*_\perp$ and $\varepsilon^*_\parallel$. The agreement between modeled and extracted results is clearly very good.

Four chicken breast samples and one beef sirloin tip sample were cut and placed within a 40×40 mm square sample holder. The sample was then placed on a CPW sensor configuration with the same line dimensions described above, formed on an FR4 laminate substrate. A 56.6-mm diameter circle was inscribed around the sensor. Eighteen radial marks were made on this circle at π/9 radian (20°) intervals. The corners of the sample holder were aligned with these marks and the two-port scattering parameters were measured at each position over the frequency range 0.5-5 GHz. The CPW sensor was first calibrated with air (ε*=1) and distilled water at 25° C. All measurements were made at room temperature, 23° C.

Table II gives the measured uniaxial permittivity tensor for the five samples at 2.45 GHz. Also included in the table are the $r^2$ values for the elliptical fits to the measured data.

The measured samples exhibit appreciable anisotropy, with $|\varepsilon^*_\perp/\varepsilon^*_\parallel|$ values ranging from 0.81 to 0.95. The high $r^2$ values show that $1/\sqrt{\varepsilon'_{meas}(\theta)}$ and $1/\sqrt{\varepsilon''_{meas}(\theta)}$ are accurately modeled by ellipses, which supports the assumption that the permittivity tensor for these materials are uniaxial.

This example demonstrates that accurate and relatively simple measurements of the uniaxial permittivity tensor of materials can be made with the technique disclosed herein. Furthermore, the suitability of this technique for measuring the anisotropic dielectric properties of semisolid materials is demonstrated. The anisotropic dielectric properties of materials measured in this way can be used to infer the difference between fresh and frozen meats, the age of meat, and properties of wood and wood products.

EXAMPLE 3

Permittivity Measurement of Biological Materials of Different Moisture Contents Measurements using the CPW were performed on samples of sawdust and gelatin of different moisture content at 25° C. The CPW was connected to an E5071C ENA Network Analyzer and a TRL calibration and two standards (air and distilled water at 25° C.) were used to calibrate the system. Results of the measurements at different frequencies are tabulated below for each material and each moisture content:

TABLE 1

Dielectric properties of sawdust at 5.7% moisture content

| | \multicolumn{6}{c}{Frequency, GHz} | | | | | |
|---|---|---|---|---|---|---|
| | 1 | 2 | 2.45 | 3 | 4 | 5 |
| $\varepsilon'$ | 1.33 | 1.30 | 1.31 | 1.29 | 1.29 | 1.28 |
| $\varepsilon''$ | 0.037 | 0.044 | 0.028 | 0.036 | 0.016 | 0.028 |

TABLE 2

Dielectric properties of sawdust at 13.1% moisture content

| | \multicolumn{6}{c}{Frequency, GHz} | | | | | |
|---|---|---|---|---|---|---|
| | 1 | 2 | 2.45 | 3 | 4 | 5 |
| $\varepsilon'$ | 1.68 | 1.59 | 1.58 | 1.56 | 1.53 | 1.50 |
| $\varepsilon''$ | 0.16 | 0.15 | 0.14 | 0.15 | 0.12 | 0.12 |

TABLE 3

Dielectric properties of sawdust at 21.4% moisture content

| | \multicolumn{6}{c}{Frequency, GHz} | | | | | |
|---|---|---|---|---|---|---|
| | 1 | 2 | 2.45 | 3 | 4 | 5 |
| $\varepsilon'$ | 2.38 | 2.27 | 2.22 | 2.18 | 2.13 | 2.03 |
| $\varepsilon''$ | 0.23 | 0.29 | 0.31 | 0.32 | 0.31 | 0.31 |

TABLE 4

Dielectric properties of sawdust at 32.0% moisture content

| | \multicolumn{6}{c}{Frequency, GHz} | | | | | |
|---|---|---|---|---|---|---|
| | 1 | 2 | 2.45 | 3 | 4 | 5 |
| $\varepsilon'$ | 4.09 | 3.84 | 3.73 | 3.61 | 3.47 | 3.27 |
| $\varepsilon''$ | 0.58 | 0.72 | 0.75 | 0.81 | 0.80 | 0.80 |

TABLE 5

Dielectric properties of sawdust at 37.6% moisture content

| | \multicolumn{6}{c}{Frequency, GHz} | | | | | |
|---|---|---|---|---|---|---|
| | 1 | 2 | 2.45 | 3 | 4 | 5 |
| $\varepsilon'$ | 4.99 | 4.67 | 4.57 | 4.41 | 4.24 | 4.01 |
| $\varepsilon''$ | 0.69 | 0.86 | 0.90 | 0.98 | 0.97 | 0.98 |

TABLE 6

Dielectric properties of gelatin slab at 78.3% moisture content

| | \multicolumn{6}{c}{Frequency, GHz} | | | | | |
|---|---|---|---|---|---|---|
| | 1 | 2 | 2.45 | 3 | 4 | 5 |
| $\varepsilon'$ | 53.9 | 51.9 | 51.1 | 49.9 | 47.8 | 45.6 |
| $\varepsilon''$ | 10.1 | 10.6 | 11.3 | 12.4 | 13.8 | 15.1 |

TABLE 7

Dielectric properties of gelatin slab at 84.5% moisture content

| | \multicolumn{6}{c}{Frequency, GHz} | | | | | |
|---|---|---|---|---|---|---|
| | 1 | 2 | 2.45 | 3 | 4 | 5 |
| $\varepsilon'$ | 60.1 | 58.3 | 57.5 | 56.1 | 54.2 | 51.7 |
| $\varepsilon''$ | 9.4 | 10.7 | 11.6 | 12.8 | 14.6 | 16.5 |

TABLE 8

Dielectric properties of gelatin slab at 93.3% moisture content

| | \multicolumn{6}{c}{Frequency, GHz} | | | | | |
|---|---|---|---|---|---|---|
| | 1 | 2 | 2.45 | 3 | 4 | 5 |
| $\varepsilon'$ | 67.8 | 66.9 | 66.0 | 64.7 | 63.2 | 60.8 |
| $\varepsilon''$ | 7.3 | 9.5 | 10.7 | 12.3 | 14.9 | 17.5 |

The foregoing detailed examples are for the purpose of illustration. Such detail is solely for that purpose and those skilled in the art can make variations therein without departing from the spirit and scope of the invention.

INDEX OF THE ELEMENTS

10. Sensor Apparatus
14. Short Planar Transmission Line
16. Long Planar Transmission Line
18. Board Top Side
19. Board Bottom Side
20. Feed Lines
22. Plated through-hole Vias
24. Microstrip-to-Coaxial line transitions 26. Sample Holder
28. Liquid Sample
30. Substrate

The invention claimed is:
1. A system for measuring a permittivity of a sample, comprising:
   A sensor apparatus comprising:
      (1) a substrate;
      (2) two straight planar transmission lines parallel to each other having different planar lengths l1 and l2 and formed on a top side of said substrate,
      (3) two feed lines formed on the bottom of said substrate, wherein said two feedlines are connected to said two straight planar transmissions lines on the top side of said substrate through a via, wherein said sensor apparatus is configured to accept a sample on the top side of said substrate that covers said two straight planar transmission lines; and
   a two port radiofrequency source and vector measurement unit connected to said feed lines via planar transmission line-to-coaxial line transitions and a first RF switch at one of the two ports and a second RF switch at the other of the two ports of said two port radiofrequeney source and vector measurement unit.

2. The system of claim 1, wherein the sensor apparatus further includes a sample holder for liquid samples so that the sample holder is placed on the substrate and covers said two straight planar transmission lines.

* * * * *